(12) United States Patent
Sohn et al.

(10) Patent No.: US 8,569,039 B2
(45) Date of Patent: Oct. 29, 2013

(54) **ETHANOL RESISTANCE *SACCHAROMYCES CEREVISIAE* GP-01 BY PROTOPLAST FUSION, METHOD FOR MANUFACTURING THEREOF, METHOD FOR MANUFACTURING YEAST CONTAINING HIGH CONTENT OF BIO ORGANIC GERMANIUM BY USING *SACCHAROMYCES CEREVISIAE* GP-01 AND HIGH WATER SOLUBLE SODIUM METAGERMANATE AS A GERMANIUM SOURCE**

(75) Inventors: Tsang-Uk Sohn, Seoul (KR); Dae-Heoun Baek, Seoul (KR)

(73) Assignee: Geranti Pharm Ltd., Seoul (KR)

( * ) Notice: Subject to any disclaimer, the term of this patent is extended or adjusted under 35 U.S.C. 154(b) by 0 days.

(21) Appl. No.: 13/132,360

(22) PCT Filed: Dec. 31, 2008

(86) PCT No.: PCT/KR2008/007834
§ 371 (c)(1),
(2), (4) Date: Jun. 2, 2011

(87) PCT Pub. No.: WO2010/064759
PCT Pub. Date: Jun. 10, 2010

(65) Prior Publication Data
US 2011/0229968 A1    Sep. 22, 2011

(30) Foreign Application Priority Data

Dec. 4, 2008 (KR) .......................... 10-2008-0122704

(51) Int. Cl.
*C12N 15/04* (2006.01)
*C12N 1/19* (2006.01)

(52) U.S. Cl.
USPC ................ 435/255.2; 435/243; 435/255.1; 435/254.1; 424/93.51

(58) Field of Classification Search
None
See application file for complete search history.

(56) References Cited

PUBLICATIONS

International Search Report for PCT/KR2008/007834.

*Primary Examiner* — Robert A Zeman
(74) *Attorney, Agent, or Firm* — The PL Law Group, PLLC

(57) ABSTRACT

A biologically pure culture of *Saccharomyces cervisiae* GP-01, and a method for producing *Saccharomyces Cervisiae* GP-01 which is ethanol-resistant and obtained by protoplast fusing *Saccharomyces Cerevisiae* (KCTC 7904) and *Candida Ethanolica* (KCTC 7181). Further, the present invention provides yeast containing the high content of organic bio-germanium (the yeast Ge-32K) and a method for producing the yeast Ge-32K, comprising adding the yeast GP-01 into a solution of sodium metagermanate ($Na_2GeO_3$) at the volume ratio of 1:0.5~2; adding 0.1~0.4 wt % of surfactant, instead of germanium dioxide as used in the prior arts; and cultivating an obtained broth. The obtained yeast Ge-32K contains the higher content of the organic bio-germanium than the conventional yeast as produced by using germanium dioxide.

4 Claims, 2 Drawing Sheets

ETHANOL RESISTANCE *SACCHAROMYCES CEREVISIAE* GP-01 BY PROTOPLAST FUSION, METHOD FOR MANUFACTURING THEREOF, METHOD FOR MANUFACTURING YEAST CONTAINING HIGH CONTENT OF BIO ORGANIC GERMANIUM BY USING *SACCHAROMYCES CEREVISIAE* GP-01 AND HIGH WATER SOLUBLE SODIUM METAGERMANATE AS A GERMANIUM SOURCE

CROSS REFERENCE TO RELATED APPLICATION AND CLAIM OF PRIORITY

The present application claims all benefits accruing under 35 U.S.C. §365(c) from the PCT International Application PCT/KR2008/007834, with an International Filing Date of Dec. 31, 2008, which claims the benefit of Korean patent application No. 10-2008-0122704 filed in the Korean Intellectual Property Office on Dec. 4, 2008, the entire contents of which are incorporated herein by reference.

BACKGROUND

1. Technical Field

The present invention relates to yeast which is ethanol resistant and contains the high content of organic bio-germanium, and the method for producing the yeast. More specifically, the method comprises producing a mutated *Saccharomyces cervisiae*, i.e., yeast GP-01 by protoplast fusion of *Saccharomyces cervisiae* (KCTC7904) and *candida ethanolica* (KCTC7181), the yeast being resistant against the high concentrate ethanol; cultivating the yeast GP-01 with sodium metagermanate ($Na_2GeO_3$) for germanium to be inoculated into the yeast GP-01 by the biotransformation; and finally obtaining a mutated yeast being ethanol-resistant and containing the high content of organic bio-germanium (hereinafter referred to as the yeast Ge-32K).

2. Background Art

Germanium is classified with organic and inorganic germanium ($GeO_2$). It is known the inorganic germanium accumulated in the human organs over the long time leads to the strong toxicity.

Organic germanium is naturally contained in microorganisms, mineral water and medicinal herbs. Further, it can be bio-synthesized in the fungal body or chemically synthesized. The organic germanium is organically bound to the proteins in the cell, peptides, etc. and the therapeutic benefits of the organic germanium for enhancing immunity; suppressing the origination and spread of the tumor cells (metastasis), treating and preventing various chronic diseases, etc. are established by numerous papers and scientific journals (Kor. J. Microbiol. Biotechnol., 2007. 35(2):118-127; J. Kor. Soc. Food Sci. Nutr. 2006. 35(6):683-689; J. Kor. Soc. Appl. Biol. Chem. 2005.48(3):246-251; Immune Network. 2006. 6(2): 86-92). In addition, the organic germanium is well-known for anticancer activities by oxygen supply to cells (J. Orthomol. Medicin., 1986. 1:145-148), purification of blood (Medicin. Hyphothesis., 1988. 26:207-215), reinforcement of immunity by activation of NK cell and macrophage (Microbiol. Immunol., 1985. 29:65-74; Kor. J. Microbiol. Biotechnol., 2007. 35(2):118-127); inducement of interferon production (Gantokagakutyoho, 9:1976-1980); suppression of generating and spreading the cancer cell (Cancer and Chemotheraphy. 1985. 12(12):2345-2351); suppression of arthritis (Autonomic & Autacoid Pharmacol. 2005. 25:129-134); prevention and treatment of various diseases such as neuralgia (Biotechnol. Appl. Biochem., 1986. 8:379-386), osteoporosis (Germanium; The health and life enhancer. 1988); mitigation of high blood pressure (hypertension) and hyperlipidemia cholesterol (Pharmacol., 1990. 41:286-291); alleviation of liver toxin (J. Kor. Soc. Food. Nutr., 1994. 23(4): 581-586); and so forth. Due to the well-known therapeutic benefits, many researches on organic germanium have been widely undertaken for decades in an attempt to apply it for treatment of various obstinate diseases such as cancer and cardiopathy, etc. in U.S.A., Japan, Europe and Korea (Anticancer Res., 1985. 5(5):479-483).

The organic germanium can be obtained by extracting from medicinal herbs like ginseng, ganoderma, etc., but such a method is difficult to be commercialized due to high cost and low productivity. Further, the organic germanium can be obtained by a chemical synthesis which includes a reaction of germanium dioxide ($GeO_2$) with organic acids, but the product obtained from the chemical synthesis comprises the inorganic germanium and thus the use for the foods or medical supplies is limited due to the un-established safety (Import Alert by US FDA, 1988).

In fact, the yeast is importantly used in baking, confectionery and brewery industry for thousands of years. Further, the yeast itself is useful as a source of nutrition for human being and attractive as a next generation protein source, a single cell protein (SCP) which is ideally comprised of protein, vitamin, mineral, etc. and characterized in the high protein and low fat.

Furthermore, the yeast is the best source of Vitamin B among the single cells and comprising lots of enzymes etc., which are mainly served in vivo metabolism. In this respect, the yeast is used as the health supplementary product. Recently, a large number of researches and developments on the health supplement products have been made so that the physiological and pharmaceutical benefits by the yeast are obtained. In order to achieve the said object, the development for the yeast containing the high contents of organic bio-germanium is highly required.

In the conventional methods, the yeast containing the organic bio-germanium is produced by cultivating the yeast in the medium including inorganic germanium ($GeO_2$). Due to the drawback that the growth of yeast is suppressed in the condition of the medium where the high content of the inorganic germanium is contained, it is difficult in the conventional methods to produce the yeast containing the appropriate amount of organic bio-germanium in aspect of the cost-effective and scale.

To remedy the above drawback, a method separately executing the process of producing the yeast in the form of a pellet and the process of inoculating germanium dioxide ($GeO_2$) in the obtained yeast is tried. However, in the above method, the yield of the palletized yeast is too low to be commercialized due to the ethanol generated during the cultivation of yeast and the content of germanium dioxide ($GeO_2$) inoculated into the yeast is extremely low.

Also it has been known that the solubility of germanium dioxide ($GeO_2$) used in the above method is 5.2 g/L at 25° C., which is served as the suppresser of the growth of yeast (J. Ind. Microbiol. Biotechnol., 1989. 4(4):299-306).

1. Therefore, it is highly required to invent the method to produce the ethanol resistant yeast containing the high content of organic bio-germanium by using the inorganic germanium which has higher solubility but much lower toxicity than germanium dioxide ($GeO_2$).

SUMMARY

It is an object of the present invention to provide a yeast GP-01 (*Saccharomyces cervisiae* GP-01, KCTC11399BP) with ethanol resistance in order to increase the yield of the yeast, and a method for producing the yeast GP-01.

It is another object of the present invention to provide a method for producing a yeast Ge-32K containing the high content of organic bio-germanium, obtained by bio-synthesis of the mutated *saccharomyces cervisiae* (ethanol resistant yeast GP-01) and sodium metagermanate ($Na_2GeO_3$).

It is a further object of the present invention to provide the yeast Ge-32K containing the high content of organic bio-germanium, obtained by bio-synthesis of the mutated *saccharomyces cervisiae* (yeast GP-01, KCTC-11399BP) and sodium metagermanate ($Na_2GeO_3$).

The present invention is related to a mutated *saccharomyces cervisiae* (yeast GP-01, KCTC11399BP) being ethanol-resistant and having an ability to produce the organic germanium and a method for producing the yeast Ge-32K containing the high content of organic bio-germanium, comprising cultivating the said yeast GP-01 with sodium metagermanate ($Na_2GeO_3$).

According to the present invention, a large number of yeast GP-01 can be produced by protoplast fusion of *saccharomyces cerevisiae* (KCTC-7904) and *candida ethanolica* (KCTC 7181). The obtained yeast GP-01 is ethanol-resistant, which enables to be cultivated under the high ethanol condition. The ethanol-resistant yeast GP-01 of the present invention can overcome the drawback of the prior arts that the growth yield of the yeast is decreased due to the ethanol generated during the cultivation of yeast.

Furthermore, as the productivity of the yeast GP-01 in cultivation is increased more than 3 times compared to that of the initial yeast (KCTC-7904), the mass-production of the yeast Ge-32K containing the high content of organic bio-germanium can be obtained by using the yeast GP-01 of the present invention.

In the process of inoculating germanium into pelletized yeast GP-01, the present invention uses sodium metagerminate ($Na_2GeO_3$) with solubility of 500 g/L, instead of germanium dioxide ($GeO_2$) commonly used in the prior arts, and thus the rate of bio-transformation of germanium in the yeast is increased owing to the higher solubility of germanium and ion transmissibility, and lower toxicity of germanium than the germanium dioxide. It is, therefore, possible for the present invention to obtain the yeast Ge-32K containing the organic bio-germanium that its contents is 2 or 3 times higher than that of the prior arts where the germanium dioxide ($GeO_2$) is used.

Also, in the process of cultivating the yeast GP-01 (KCTC11399BP) with sodium metagerminate ($Na_2GeO_3$), the present invention adds surfactant for the organic bio-germanium to be more effectively inoculated into the pelletized yeast by the biotransformation.

DETAILED DESCRIPTION

Figure 1:
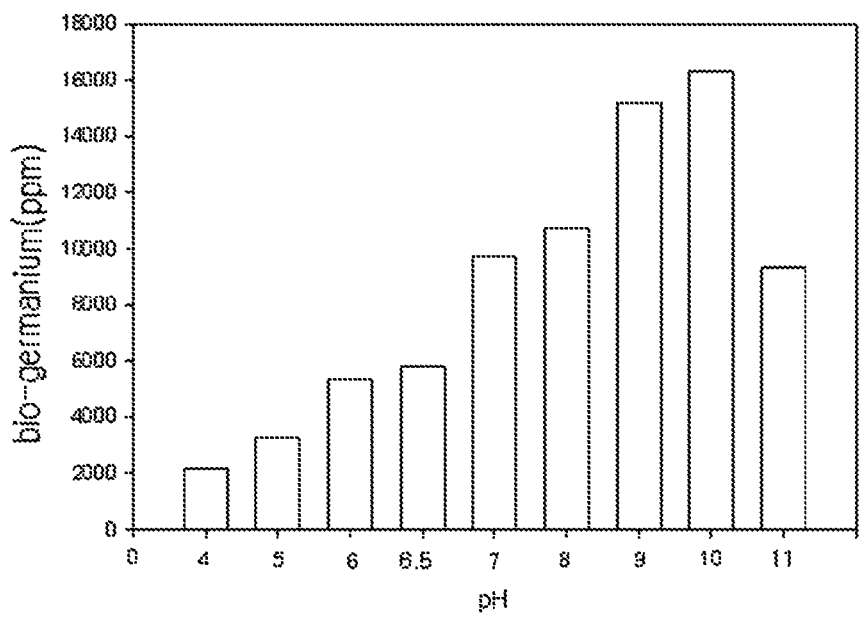
FIG. 1 is a graph showing the bio-germanium content in the yeast GP-01 of the present invention according to the variation of pH.

According to an embodiment of the present invention relates to a mutated *Saccharomyces cervisiae*, i.e., yeast GP-01 (KCTC11399BP) having an ability to produce the organic germanium.

The mutated *Saccharomyces cervisiae*, yeast GP-01 was duly deposited in Korea Collection for Type Culture of Korea Research Institute of Bioscience and Biotechnology (having the address of KRIBB, Gwahak-lo-111, Yuseong-gu-Daejeon 305-808, Republic of Korea) under the Access number of KCTC 11399BP on Oct. 7, 2008.

More specifically, the embodiment of the present invention provides the mutated *Saccharomyces cervisiae* (yeast GP-01, KCTC 11399BP) with ethanol-resistance, wherein the method includes protoplast fusion of *Saccharomyces cervisiae* (KCTC7904) with *candida ethanolica* (KCTC7181) having the effective utilization of ethanol.

Further, an embodiment of the present invention provides the yeast Ge-32K containing the high content of organic bio-germanium, which can be produced by cultivating the yeast GP-01 with sodium metagermanate ($Na_2GeO_3$) solution so as for the germanium to be inoculated into the yeast by bio-transformation.

The mutated yeast can be obtained by protoplast fusion of *Saccharomyces cervisiae* (KCTC7904) and *candida ethanolica* (KCTC7181) with a mixed solution of 1M sorbitol as osmotic pressure stabilizer and 0.5 M of 2-mercaptoethanol as reducing agent.

And, the protoplast can be obtained by suspending the pelletized yeast in sorbitol solution, to which a cell wall hydrolase is added, to resolve the cell wall. In this case, the preferable volume ratio of 1 M sorbitol and 2-mercaptoethanol is 1: 2-4, more preferably, 1: 2-3.

Also, the protoplast fusion is accomplished by adding two protoplasts of *Saccharomyces cervisiae* (KCTC7904) and *candida ethanolica* (KCTC7181) into the mixed solution comprised of polyethylene glycol (MW 4000); 10 mM of calcium chloride ($CaCl_2$); and one selected among 1 M sorbitol, sucrose and mannitol.

In this case, the preferable volume ratio of the one selected solution (1 M sorbitol), polyethylene glycol and calcium chloride ($CaCl_2$) is 1:2-4:2-5, more preferably, 1:2-3: 2-4.

An embodiment of the present invention provides a method for producing the yeast Ge-32K containing the high content of organic bio-germanium. The method is comprised of cultivating the yeast GP-01 with sodium metagermanate ($Na_2GeO_3$).

The preferable volume ratio of the yeast GP-01(KCTC 11399BP) and sodium metagermanate ($Na_2GeO_3$) is 1:0.5-2, more preferably, 1:1.

In addition, it is preferable to cultivate the yeast GP-01 (KCTC 11399BP) with sodium metagermanate ($Na_2GeO_3$) for 19-21 hours at pH 9~10 and temperature 3~40° C. in order for the germanium to be inoculated into the yeast by the bio-transformation. The above cultivating step may be accomplished by the ordinary method of cultivating yeast.

By the said method of the present invention, the yeast Ge-32K containing relatively high content of organic bio-germanium can be obtained.

Hereinafter, the more detailed methods of the present invention for producing the yeast GP-01 with ethanol-resistance and for producing the yeast Ge-32K containing the high content of organic bio-germanium are provided.

1$^{st}$ Process: Producing a protoplast fused yeast with ethanol-resistance

A protoplast fused yeast was obtained by fusing and cultivating two protoplasts of *Saccharomyces cervisiae* (KCTC7904) and *candida ethanolica* (KCTC7181), which were deposited at Korea Collection for Type Culture (KCTC) of Korea Research Institute of Bioscience and Biotechnology.

In more detail, *Saccharomyces cervisiae* (KCTC7904) and *candida ethanolica* (KCTC7181) were cultivated, respectively. The obtained culture mediums were centrifuged to obtain the pelletized yeasts.

It is preferable for the centrifugations of the culture mediums to be carried out when the optical density (O.D.) of the culture mediums is 0.45~0.50 at early logarithmic phase. The palletized yeasts can be obtained from either each of the mediums of the strains or one medium where the two strains are cultured together.

At the volume ratio of 1:1, the two pelletized yeasts were added in a solution, which 1 M of sorbitol and 0.5 M of 2-mercaptoethanol are mixed, in order to wash the yeasts twice. The washed yeasts were left during the pre-determined period and then, a solution containing cell wall hydrolase was added to a broth (containing palletized yeasts, 1M of sorbitol and 0.5 M of 2-mercaptoethanol) at the volume ratio of 1:1 The yeasts were suspended in the broth to produce protoplasts.

1 M sorbitol, polyethylene glycol (MW 4000) and 10 mM of calcium chloride ($CaCl_2$) were added to the broth for the protoplast to be fused. Finally, the broth was centrifuged to obtain the protoplast fused yeasts.

The protoplast fused yeast was cultivated at an agar culture medium for 6~8 days and staining them to identify the protoplast fused yeast. After the protoplast fused yeast was confirmed by the staining, a single colony was collected.

Preferably, the used agar culture medium is composed of 3~5 wt % of yeast extract, 7~9% of peptone, 7~9 wt % of glucose, 0.1~0.6 wt % of calcium chloride, 72~75 wt % of sorbitol and 5~8 wt % of agar, but is not limited to the above. Any agar conventionally used in the art can be also applied.

$2^{nd}$ Process: Producing the ethanol resistant yeast which has a high adaptability against a high concentration of germanium (yeast GP-01, (KCTC 11399BP)), and manufacturing a solution of sodium metagermanate ($Na_2GeO_3$).

The protoplast fused yeast as obtained from the $1^{st}$ process was cultivated in the medium containing sodium metagermanate ($Na_2GeO_3$) to enhance the adaptability against the high concentration of germanium of the yeast.

In order to produce the yeast GP-01 (KCTC 11399BP), sodium metagermanate ($Na_2GeO_3$) was used for the germanium-adaptability. The protoplast fused yeast as obtained from the $1^{st}$ process was cultivated in liquid culture medium with 3,000~20,000 ppm of the germanium for 10~13 hour.

Preferably, the liquid culture medium is composed of 6~10 wt % of ethanol, 0.1~0.5 wt % of peptone, 0.1~0.4 wt % of yeast extract, 2~5 wt % of glucose, 0.1~0.4 wt % of malt extract and 84~90 wt % of water, but is not limited to the above.

Preferably, the optimum concentration of ethanol is 8~10 wt % and the content of germanium in sodium metagermanate ($Na_2GeO_3$) is 3,000~10,000 ppm in the liquid culture medium.

In case where the concentration of ethanol is less than 6 wt % or over 10 wt %, it may lead to the difficulties with obtaining the optimum quantity of the yeast or collecting the ethanol resistant yeast efficiently. Further, in case where the content of germanium is less than 3,000 ppm in sodium metagermanate ($Na_2GeO_3$), it is difficult to collect the yeast containing the high content of germanium effectively and in case where the content of germanium is over 10,000 ppm in sodium metagermanate ($Na_2GeO_3$), it is also difficult to obtain the cost-effective yield.

In the liquid culture medium, the yeasts which are actively-grown and have the lower content of germanium in the supernatant of the culture were collected. The collected yeasts were sub-cultured in a plate medium to isolate and obtain a mutated *Saccharomyces cervisiae*, i.e., yeast GP-01(KCTC 11399BP).

As the obtained yeast GP-01 has the high resistance against ethanol, it is possible for the yield of the yeast to be increased.

Preferably, the plate medium as used above was composed of 3~5 wt % of agar, 10~12 wt % of yeast extract, 20~23 wt % of peptone, 20~23 wt % of glucose and 39~42 wt % of ethanol, wherein the ethanol was added before solidifying the plate, but is not limited to the above.

The prepared plate was double sealed at the room temperature to prevent ethanol from being evaporated, after the sub-culture of the yeasts.

Sodium metagermanate ($Na_2GeO_3$) used as the inorganic germanium in the present invention was synthesized by adding germanium dioxide into one of sodium carbonate ($Na_2CO_3$), calcium carbonate ($CaCO_3$), potassium carbonate ($K_2CO_3$) or potassium bicarbonate ($KHCO_3$) at the equivalent ratio, and sterilizing it. The obtained sodium metagermanate ($Na_2GeO_3$) is a germanium solution with high solubility and should be prepared, immediately prior to the use in the biological transformation process.

The $2^{nd}$ Process of the present invention, in order for the yeast to be mutated, may further include radiation of gamma rays ($Co^{60}$) of 2.0~2.5 KGy ($D_{10}$ value) for 2~4 hours into the protoplast fused yeast before culturing the yeast in the medium containing sodium metagerminate ($Na_2GeO_3$).

Where the gamma rays ($Co^{60}$) radiation is less than 2.0 KGy, it may be difficult to obtain the desired mutated yeast because of too much colonies of the mutated strains formed on the plate. And, where gamma rays ($Co^{60}$) radiation is more than 2.5 KGy, it may be also difficult to obtain the desired mutated yeast because of too high extinction rate of the yeast.

The mutated yeast that is irradiated by gamma rays ($Co^{60}$) as mentioned above can be used for the subculture after culturing it in the YM broth for 1 hour and stabilizing the same.

$3^{rd}$ Process: Inflow of inorganic germanium ion into the yeast GP-01

The yeast GP-01 as obtained in the $2^{nd}$ process was cultivated with the solution of sodium metagermanate ($Na_2GeO_3$) for the yeast containing the high content of organic bio-germanium to be produced.

In order to produce the yeast containing the high content of organic bio-germanium (the yeast Ge-32K), the culture medium prepared in the $2^{nd}$ process was centrifuged to collect the yeast only. And, the medium containing the germanium was prepared by inserting the collected yeast into the solution of sodium metagermanate ($Na_2GeO_3$) where the content of germanium is 3,000~10,000 ppm.

The volume ratio of the added yeast and the solution of sodium metagermanate ($Na_2GeO_3$) is 1:0.5~2.0.

The obtained medium containing germanium was cultivated for 19~21 hours at pH 9~10 and 30~40° C. after adding the 0.01~0.04 wt % of surfactant Thus, the yeast containing high content of organic bio-germanium (the yeast Ge-32K) of an embodiment of the present invention was produced.

The added surfactant can lead to increasing the content of germanium in the cell by the increased permeability of the cell membrane. Thus, it is possible for the inorganic germanium to be inoculated into the mutated yeast, i.e., yeast GP-01 (KCTC 11399BP).

Preferably, the surfactant used in an embodiment of the present invention is Twin-80, but is not limited to the above.

Where the mixing ratio of the yeast and the solution of sodium metagermanate ($Na_2GeO_3$) is less than 1:0.5 or over 1:2, it may lead to decreasing content of bio-germanium in the yeast due to the high viscosity of the suspension including the yeast and the lower diffusion speed between germanium and yeast cell walls.

Further, where the value of pH is less than 9 or over 10, or the temperature is below 30° C. or over 40° C., it may lead to decreasing the contents of bio-germanium in the yeast.

In addition, where the surfactant is added in the culture medium containing germanium at less than 0.1 wt %, the permeability of the cell wall is poor. Also, where the surfactant is added in the culture medium at over 0.4 wt %, the permeability of membrane is inhibited as the structure of the yeast cell walls is broken so that the contents of bio-germanium in the yeast may be decreased to the same contents of bio-germanium as the case where the surfactant is not added.

After producing the yeast containing the high content of organic bio-germanium, i.e., the yeast Ge-32K, by using the mutated *Saccharomyces cervisiae*, i.e., yeast GP-01, the remaining medium containing the germanium can be re-used by filtering with 0.2 μm membrane filter.

In order to assist your understanding on the present invention, exemplary embodiments of the present invention will be described in more detail as follows. However, the following examples are proposed for illustrative purposes and those skilled in the art will appreciate that various modifications, additions and/or substitutions are possible without departing from the scope and spirit of the invention which is defined in the accompanying claims and their equivalents.

PREPARATION EXAMPLE 1

Preparing of Sodium Metagermanate ($Na_2GeO_3$) Solution

The solution of Sodium Metagermanate ($Na_2GeO_3$) was prepared by dissolving sodium carbonate ($Na_2CO_3$, Kanto, Japan) in water, adding germanium dioxide ($GeO_2$, PPM GmbH, Germany) at the equivalent ratio of 1:1 against the said sodium carbonate, and sterilized the obtained solution.

The solubility of the solution of Sodium Metagermanate ($Na_2GeO_3$) prepared as above is quite high, 500 g/L (25° C.).

Example 1

Producing of Protoplast Fused Yeast and of Ethanol Resistant Yeast by Using the Protoplast Fused Yeast

*Saccharomyces Cerevisiae* (KCTC 7904) and *Candida Ethanolica* (KCTC7181) provided by Korea Collection of Type Culture (KCTC) were cultivated at an Erlenmeyer flask containing YPD culture medium for 10 hours at 30° C. The prepared culture medium was centrifuged at the early logarithmic phase to collect the yeast when the UV spectrophotometer of the yeast is 0.5. The collected yeast was washed two times with the sterilized physiological saline.

The washed yeast was suspended in a solution where 1M sorbitol and 0.5M mercapto ethanol are mixed at the volume ratio of 1:2 (the suspension ratio between the yeast and the solution is 1:1) for 30 minutes at 30° C. And then, the solution including the yeast was washed by the centrifuge.

Then, 200 units of a cell wall degrading enzyme, zymolase (L4025, sigma, USA) was added to the centrifuge-washed solution (containing the yeast, 1M sorbitol and mercapto ethanol) at the ratio of 1:1. The obtained solution was suspended for 1 hour at 30° C. to produce the protoplast of the yeast.

A solution of 1M sorbitol, polyethylene glycol (MW 4000) and 10 mL of sodium chloride ($CaCl_2$) at the volume ratio of 1:3:2 was added in the above solution containing the protoplast fused yeast at the equivalent ratio. The mixed solution was fused for 30 minutes at 30° C. to produce the protoplast fused yeast of an embodiment of the present invention.

In order to separate the protoplast fused yeast, the protoplast fused yeast was cultivated for 1 week in SOS solid culture medium containing 4.1 wt % of yeast extract, 8.1 wt % of peptone, 8.1 wt % of glucose, 0.4 wt % of sodium chloride, 73.2 wt % of sorbitol and 6.1 wt % of agar. After the 1 week cultivation, the yeast was separated by staining it with carbol fuchin.

The separated yeast was cultivated for 10 hours in the YM liquid medium containing 10 wt % of ethanol, 0.4 wt % of peptone, 0.2 wt % of yeast extract, 4 wt % of glucose, 0.2 wt % of malt extract and 85.2 wt % of water after adding 30 wt % of solution of sodium metagermanate ($Na_2GeO_3$) containing 10,000 ppm of germanium.

In the liquid culture medium, the yeasts which are actively-grown and have the lower content of germanium were collected in the supernatant of the culture. The collected yeasts were subcultured in a plate medium containing 4.1 wt % of agar (Difco), 11.1 wt % of yeast extract (Genico, Korea), 22.0 wt % of peptone (Difco), 22.0 wt % of glucose (Daesang, Korea) and 40.8 wt % of ethanol to isolate and obtain the mutated *Saccharomyces cervisiae*, i.e., yeast GP-01 (KCTC 11399BP).

In order to examine the ethanol resistance of the obtained yeast GP-01, the ethanol, which is the inhibitor of the growth, was added by the concentrations and the status of the growth of the yeast was checked.

Following Table 1 shows the status of growth of the yeast according to ethanol concentrations by measuring the growth three times for each ethanol concentration for accuracy.

TABLE 1

| Concentration of ethanol (%, v/v) | KCTC7904 OD(660 nm, 1/20) | Growth status of The yeast GP-01 (1$^{st}$ investigation) OD(660 nm, 1/20) | GP-01 (2nd) OD(660 nm, 1/20) | GP-01 (3$^{rd}$) OD(660 nm, 1/20) |
|---|---|---|---|---|
| 0 | 0.10 | 0.10 | 0.13 | 0.12 |
| 6.0 | 0.07 | 0.15 | 0.14 | 0.20 |
| 8.0 | 0.06 | 0.14 | 0.20 | 0.23 |
| 10.0 | 0.05 | 0.16 | 0.19 | 0.24 |
| 15.0 | — | 0.12 | 0.08 | 0.15 |

Ethanol is generated while the microorganism is cultivated, but inhibits their growth.

As shown in the above Table 1, the growth rate of the mutated *Saccharomyces cervisiae*, yeast GP-01(KCTC 11399BP) was increased in the presence of ethanol upon comparing the case in the absence of ethanol. In case where the concentration of ethanol was 6-10%, the best growth rate of the yeast GP-01 was obtained.

In this respect, according to an embodiment of the present invention, the ethanol-resistant yeast, i.e., yeast GP-01 (KCTC 11399BP) which has the increased growth rate even in the presence of ethanol can be obtained.

Furthermore, upon comparing the yield of the yeast GP-01 of an embodiment of the present invention with the yield of initial yeast (*Saccharomyces Cerevisiae*, KCTC 7904), the yield of the yeast GP-01(KCTC-11399BP) of an embodiment of the present invention was more than 3 times increased.

Example 2

Change of Contents of Germanium in Yeast GP-01 by Concentrations of the Solution of Sodium Metagermanate ($Na_2GeO_3$)

The broth medium containing the mutated *Saccharomyces Cerevisiae*, yeast GP-01 (KCTC11399BP), was centrifuged to collect the palletized yeast. The collected pelletized yeast was added in each of the solutions of sodium metagermanate ($Na_2GeO_3$) with different concentrations of germanium. The prepared solutions were cultivated for 20 hours at pH 10 and temperature 40° C.

In order to determine the content of bio-germanium in the yeast GP-01, 1 g of the cultivated and dried yeast GP-01 was added in 30 ml of nitric acid. The obtained sample was heated to be decomposed. After adjusting pH value to 6, 1 ml of the sample was mixed with 1 ml of phenylfluorone and 1 ml of cyclo nucleic acid. The obtained sample was stationary for 30 hours at 30° C. and then determined the content of germanium in the yeast GP-01 by using UV spectrophotometer at 525 nm.

Also, as a control, the same procedure described in Example 2 was performed, except that a solution of germanium dioxide ($GeO_2$) was used instead of sodium metagermanate ($Na_2GeO_3$).

Following Table 2 shows the comparison of the content of bio-germanium inoculated into the yeast GP-01 and the initial *Saccharomyces Cerevisiae* (KCTC 7904) according to the content of germanium in the solutions of sodium metagermanate ($Na_2GeO_3$) vs the solution of germanium dioxide ($GeO_2$).

The contents of germanium in the yeast GP-01 (KCTC 11399BP) was measured by the same method as Example 2.

Table 3 shows the comparison of the bio-germanium contents in the yeast GP-01 (KCTC 11399BP) by the mixing ratios of the yeast and germanium dioxide ($GeO_2$), and the yeast and sodium metagermanate ($Na_2GeO_3$).

TABLE 2

| Contents of Germanium in the solution (ppm) | Bio-germanium content inoculated into the yeast GP-01 (ppm) | | | | | | | |
|---|---|---|---|---|---|---|---|---|
| | $GeO_2$ solution | | | | $Na_2GeO_3$ solution | | | |
| | | | Yield (%) | | | | Yield (%) | |
| | KCTC7904 | GP-01 | KCTC7904 | GP-01 | KCTC7904 | GP-01 | KCTC7904 | GP-01 |
| 1,000 | 780 | 870 | 78 | 87 | — | — | — | — |
| 2,000 | 870 | 1,786 | 44 | 89 | — | — | — | — |
| 3,000 | 980 | 2,670 | 33 | 89 | 950 | 4,640 | 32 | 155 |
| 4,000 | 1,430 | 3,850 | 36 | 96 | 1,500 | 6,840 | 38 | 171 |
| 5,000 | 1,500 | 4,753 | 30 | 95 | 2,370 | 9,700 | 47 | 194 |
| 10,000 | — | — | | | 4,500 | 13,000 | 45 | 130 |
| 15,000 | — | — | | | 5,730 | 16,500 | 38 | 110 |

Upon comparing the amounts of the inoculated bio-germanium by the solutions, Table 2 shows that in case where the amounts of germanium in the solutions are the same, the more amounts of the bio-germanium were inoculated into the yeasts in the solution of sodium metagermanate($Na_2GeO_3$) than that in the solution of germanium dioxide ($GeO_2$) solution.

Also, upon comparing the amount of the inoculated bio-germanium by the yeasts, Table 2 shows that the more amount of the bio-germanium was inoculated into the mutated *Saccharomyces Cerevisiae* (yeast GP-01, KCTC 11399BP) of the present invention, than the initial *Saccharomyces Cerevisiae* (KCTC 7904).

Where the content of germanium in sodium metagermanate ($Na_2GeO_3$) is 3,000~10,000 ppm, the most amount of inorganic germanium ion was inoculated into the yeasts. In addition, where the content of germanium in the solution is 5,000 ppm, the yield of the germanium to be inoculated reached the highest.

Example 3

Comparison of the Content of the Inoculated Bio-Germanium in the Yeast GP-01 According to the Mixing Ratio Between the Palletized Yeast and the Solution of Inorganic Germaniums ($GeO_2$ and $Na_2GeO_3$)

The broth containing the ethanol-resistant yeast GP-01 as prepared in the Example 1 was centrifuged to collect the yeast. The collected yeast was added in the solutions which contain sodium metagermanate ($Na_2GeO_3$) and germanium dioxide but have different mixing ratios of the said sodium metagermanate ($Na_2GeO_3$) and germanium dioxide. The obtained solutions were cultivated for 20 hours at pH 10 and temperature 40° C.

Also, as a control, the same procedure described in Example 3 was performed, except that a solution of (inorganic) germanium dioxide ($GeO_2$) was used instead of sodium metagermanate ($Na_2GeO_3$).

TABLE 3

| Mixing ratio | Bio-germanium content in yeast GP-01 (ppm) | |
|---|---|---|
| (yeast GP-01:Ge solution) | $GeO_2$ Solution | $Na_2GeO_3$ Solution |
| 1:0.2 | 1,920 | 4,350 |
| 1:0.5 | 5,670 | 14,800 |
| 1:1 | 4,780 | 12,600 |
| 1:2 | 2,500 | 9,760 |
| 1:3 | 1,700 | 8,720 |

Table 3 shows that the most amounts of bio-germanium were inoculated into the yeast where the mixing ratio between the yeast and the inorganic germanium is 1:0.5~2. Further, the content of bio-germanium was increased more than 2-4 times when adding sodium metagermanate ($Na_2GeO_3$) solution than adding inorganic germanium (germanium dioxide).

Example 4

Optimal Conditions for Inoculating Inorganic Germanium Ion into the Yeast

The broth containing the ethanol-resistant yeast GP-01 as prepared in the Example 1 was centrifuged to collect the yeast. At the ratio of 1:0.5, the collected yeast was added in the solution of sodium metagermanate ($Na_2GeO_3$) having 5,000 ppm of germanium. After adding surfactant (Twin-80), the obtained solution was cultivated for 20 hours by various conditions for pH, temperature or the broth containing germanium.

The pH was regulated by using 1N NaOH, and a number of tests were repeatedly performed under different temperatures and concentrations of surfactant.

When measuring the content of germanium, the broth without adding the surfactant was used as a control.

The measurement of content of bio-germanium in the yeast GP-01 (KCTC11399BP) of the present invention was made by the same method as Example 2.

Table 4 shows the amounts of germanium ion inoculated into the yeast by the variation of pH, temperature and concentration of surfactant (Twin-80).

TABLE 4

| pH | Bio-germanium inoculated (ppm) | temperature (° C.) | Bio-germanium inoculated (ppm) | Concentration of Surfactant (Twin-80, wt %) | Bio-germanium inoculated (ppm) |
|---|---|---|---|---|---|
| 4.0 | 2,190 | 20 | 3,102 | Control | 1,720 |
| 5.0 | 3,254 | 30 | 9,648 | 0.1 | 8,743 |
| 6.0 | 5,320 | 35 | 13,250 | 0.2 | 16,250 |
| 6.5 | 5,790 | 40 | 14,700 | 0.3 | 12,530 |
| 7.0 | 9,750 | 45 | 8,350 | 0.4 | 9,670 |
| 8.0 | 10,700 | 50 | 4,564 | 0.5 | 7,624 |
| 9.0 | 15,200 | — | — | 0.6 | 5,670 |
| 10.0 | 16,300 | — | — | 0.7 | 4,830 |
| 11.0 | 9,320 | — | — | 0.8 | 2,700 |

Table 4 shows the optimum condition to inoculate the inorganic germanium into the yeast is comprised of pH 8~10, temperature at 30~40° C., and 0.1~0.4 wt % of surfactant in the broth containing germanium, more preferably, pH 10, temperature at 40° C. and 0.2 wt of surfactant.

Figure 2:
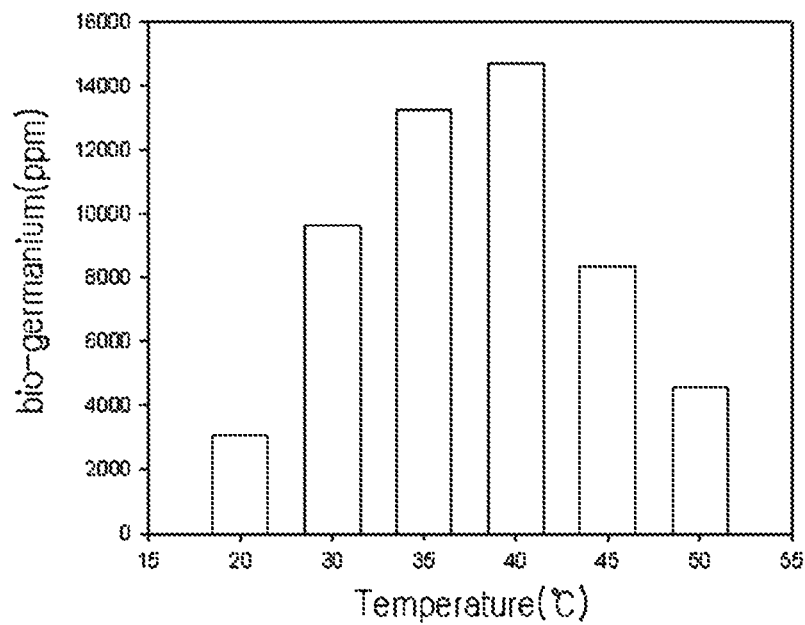
FIG. 2 is a graph showing the bio-germanium content in the yeast GP-01 of the present invention according to the change of temperature.
Figure 3:
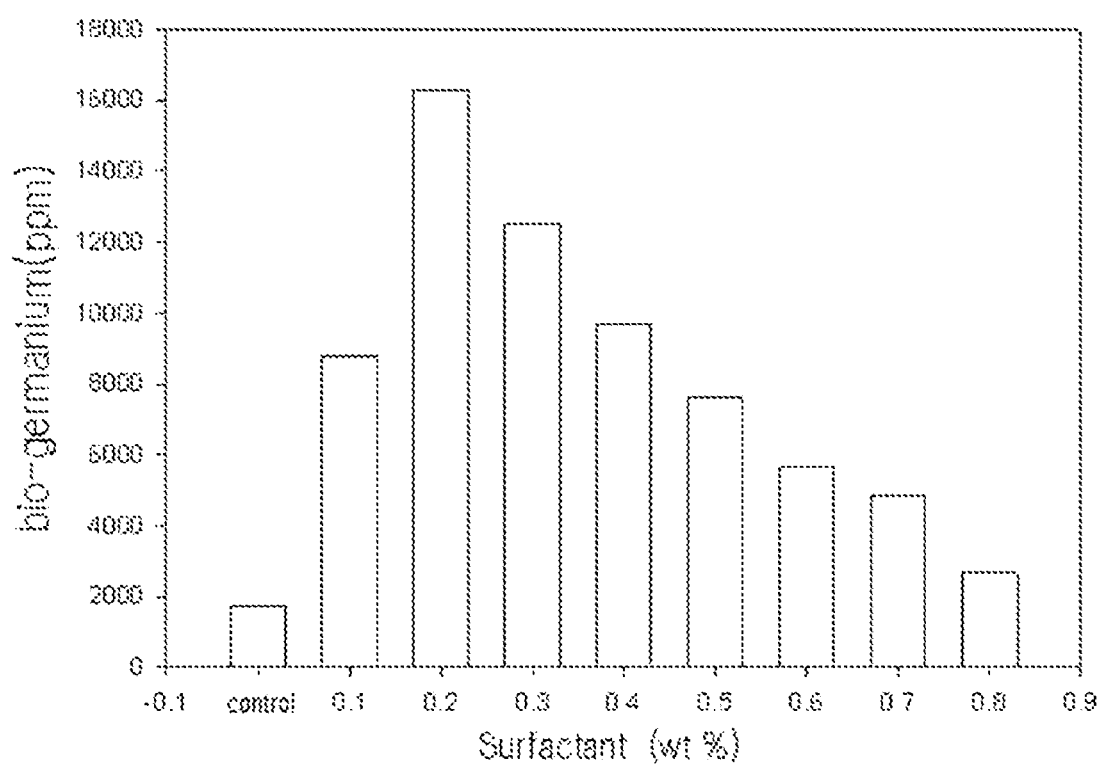
FIG. 3 is a graph showing the bio-germanium content in the yeast GP-01 of the present invention according to the variation of concentration of surfactant in wt %.

Variation of the content of inoculated bio-germanium by pH, temperature and the concentration of inorganic germanium can be shown in FIGS. 1, 2 and 3.

BUDAPEST TREATY ON THE INTERNATIONAL RECOGNITION OF THE DEPOSIT OF
MICROORGANISMS FOR THE PURPOSE OF PATENT PROCEDURE

INTERNATIONAL FORM

RECEIPT IN THE CASE OF AN ORIGINAL
Issued pursuant to Rule 7.1 by the
INTERNATIONAL DEPOSITARY AUTHORITY
Identified at the bottom of this page To GERANTI PHARM LTD.
Gwansan-ri 320-14, Jupo-myeon
Borlyeong-si, Chungcheongnam-do 355-831
Republic of Korea

| I. IDENTIFICATION OF THE MICROORGANISAM | |
|---|---|
| Identification reference given by the DEPOSITOR: | Accession number given by the INTERNATIONAL DEPOSITARY AUTHORITY: |
| *Saccharomyces cerevisiae var* GP-01 | KCTC 11399BP |
| II. SCIENTIFIC DESCRIPTION AND/OR PROPOSED TAXONOMIC DESIGNATION | |
| The microorganism identified under I above was accompanied by: [x] a scientific description [ ] a proposed taxonomic designation (Mark with a cross where applicable) | |
| III. RECEIPT AND ACCEPTANCE | |
| This International Depository Authority accepts the microorganism identified under I above, which was received by it on October 7, 2008. | |
| IV. RECEIPT OF REQUEST FOR CONVERSION | |
| The microorganism identified under I above was received by this International Depository Authority on October 7, 2008 and a request to convert the original deposit to a deposit under Budapest Treaty wa received by it on (date of receipt of request for conversion). | |
| V. INTERNATIONAL DEPOSITARY AUTHORITY | |
| Name: Korean Collection for Type Culture  Address: KRIBB, Gwahak-lo 111 Yuseong-gu, Daejeon 305-806 Republic of Korea | Signature(s) of person (s) having the power to represent the International Depository Authority or of authorized official (s):  Name: Oh Hee-mok Date: October 14, 2008 |

Confirmed that the attached translation is true to the original on
December 17, 2008 by DARAE PATENT FIRM

The invention claimed is:

1. A method for preparing a yeast Ge-32K comprising adding *Saccharomyces cerevisiae* GP-01, which was deposited with the Korea Collection for Type Culture of Korea Research Institute of Bioscience and Biotechnology under the accession number KCTC 11399BP, to a culture medium containing sodium metagermanate (Na2GeO3) and culturing the *Saccharomyces cerevisiae* GP-01 in the culture medium containing the sodium metagermanate (Na2GeO3).

2. The method according to claim 1, wherein the sodium metagermanate (Na2GeO3) is prepared by (i) dissolving either sodium carbonate (Na2CO3), calcium carbonate (CaCO3) or potassium bicarbonate (KHCO3) in water and adding germanium dioxide (GeO2) to the solution prepared by said (i) at an equivalent volume ratio.

3. The method according to claim 1, wherein a mixing volume ratio between the *Saccharomyces cervisiae* GP-01 and the culture medium containing the sodium metagermanate ($Na_2GeO_3$) is 1:0.5-2.0.

4. The method according to claim 2, wherein the culturing is performed for 19~21 hours at pH 9~10 and temperature 30~40° C.

* * * * *